United States Patent [19]

Hickmann et al.

[11] 4,007,209

[45] Feb. 8, 1977

[54] ACETALS WHICH ACT AS PHOTOINITIATORS

[75] Inventors: Eckhard Hickmann, Ludwigshafen; Martin Fischer, Ellerstadt; Otto Volkert; Mong-Jon Jun, both of Ludwigshafen, all of Germany

[73] Assignee: Badische Anilin- & Soda-Fabrik Aktiengesellschaft, Ludwigshafen (Rhine), Germany

[22] Filed: Mar. 10, 1975

[21] Appl. No.: 557,046

Related U.S. Application Data

[63] Continuation of Ser. No. 375,176, June 29, 1973, abandoned.

[30] Foreign Application Priority Data

July 1, 1972 Germany .......................... 2232497

[52] U.S. Cl. .......................... 260/345.9; 260/590 D; 260/347.8; 204/159.23; 96/35.1
[51] Int. Cl.$^2$ ...................................... C07D 309/08
[58] Field of Search ........ 260/345.9, 347.8, 611 A, 260/590

[56] References Cited

UNITED STATES PATENTS 2,541,747   2/1951   Copelin ............................ 260/333

FOREIGN PATENTS OR APPLICATIONS 1,265,604   3/1972   United Kingdom

OTHER PUBLICATIONS

H. G. Heine et al., Angew. Chem. internat. Edit., vol. 11 (1972) No. 11, pp. 974–978.
A. C. Ott et al., Jour. Am. Chem. Soc., vol. 74 (1952) pp. 1239–1241.

*Primary Examiner*—Norma S. Milestone
*Attorney, Agent, or Firm*—Johnston, Keil, Thompson & Shurtleff

[57] ABSTRACT

The invention relates to special acetals of benzoin compounds which act as photoinitiators, and to a technically simple manufacturing process involving the reaction of an appropriate $\alpha$- or $\beta$-hydroxyketone with an $\alpha,\beta$-olefinically unsaturated ether in the presence of an acid catalyst. The acetals are particularly suitable for use as photoinitiators in the preparation of photopolymer printing plates.

5 Claims, No Drawings

ACETALS WHICH ACT AS PHOTOINITIATORS

This is a continuation of application Ser. No. 375,176 filed June 29, 1973, and now abandoned.

The invention relates to acetals which act as photoinitiators and have the structure of previously unknown benzoin compounds.

The use of various benzoin derivatives has already been disclosed. However, the derivatives which are suitable for use as photoinitiators are not easily obtainable.

The present invention relates to new acetals of benzoin compounds which can be manufactured simply and in high yields and which act as photoinitiators; they have the formula

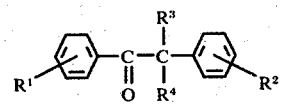

which contains at least one acetal group

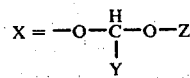

in the radicals $R^3$ or $R^4$, Y being $CH_3$ and Z being $C_2$–$C_4$-alkyl, or Y and Z together being 1,3-alkylene or 1,4-alkylene with 3 or 4 carbon atoms, which are optionally substituted by $C_1$–$C_4$-alkoxy; $R^1$ and $R^2$ are H, $C_1$–$C_4$-alkyl, $C_1$–$C_4$-alkoxy or Cl, $R^3$ is H, $CH_3$, $OCH_3$, $CH_2OR^5$ or $CH_2X$, $R^4$ is X or $OR^5$ and $R^5$ is $C_1$–$C_6$-alkyl.

The invention further relates to a process for the manufacture of acetals of benzoin compounds which act as photoinitiators, by reaction of an α- or β-hydroxyketone of the formula

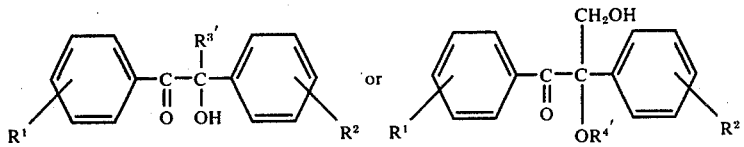

in which $R^1$ and $R^2$ are H, $C_1$–$C_4$-alkyl, $C_1$–$C_4$-alkoxy or Cl, $R^{3'}$ is H, $CH_2OH$, alkyl, alkoxy or alkoxymethyl and $R^{4'}$ is alkyl, with an α,β-olefinically unsaturated ether in an aprotic solvent, for example benzene, toluene, diethyl ether, dioxane or tetrahydrofuran at temperatures between about −10° and +100° C, preferably at about 20° to 60° C or at the boiling point of the solvent, in the presence of an acid catalyst such as concentrated sulfuric acid, boron trifluoride etherate and especially p-toluenesulfonic acid. The α,β-olefinically unsaturated ether by itself can also, where appropriate, be used as the solvent. After the reaction, the acid catalyst is removed or converted into a salt with a base, such as potassium carbonate, and separated, as the salt, from the reaction product. The invention further relates to the use of the new products as photoinitiators and especially in the manufacture of photopolymer printing plates.

By way of example, the process can be represented by the following equations:

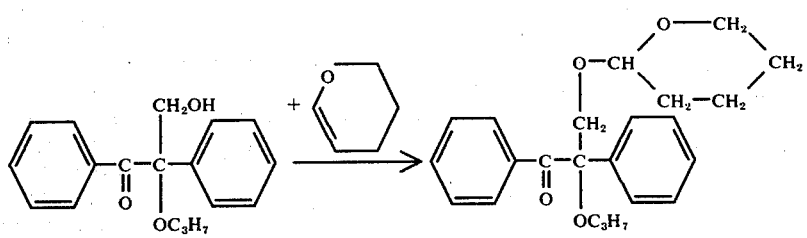

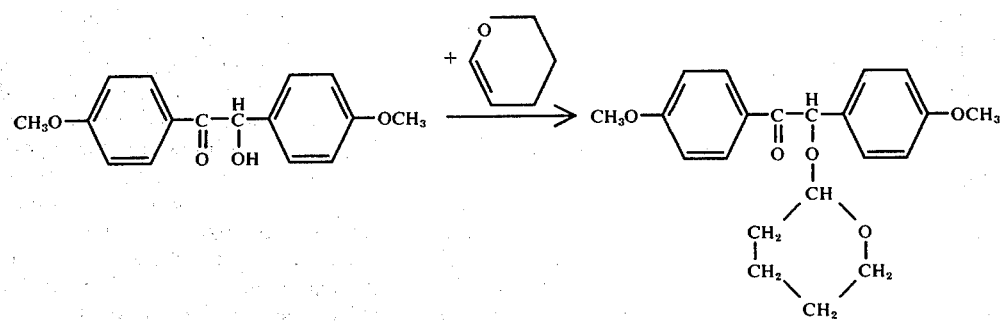

-continued

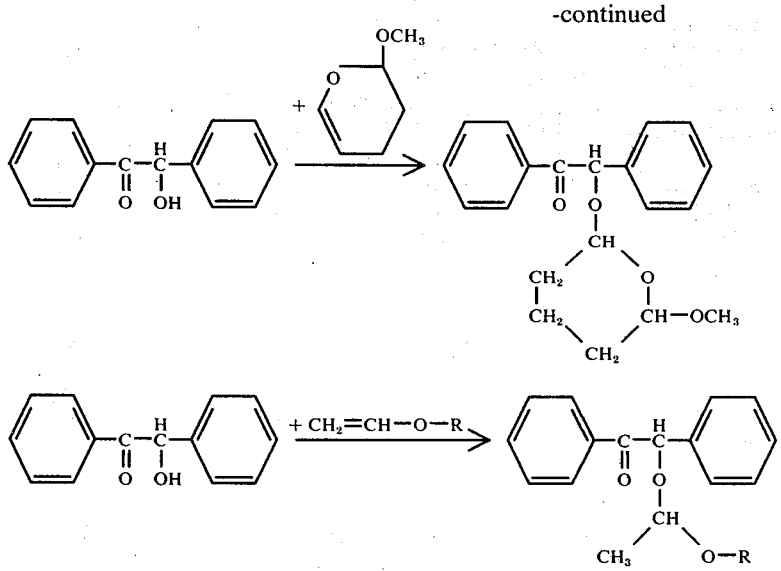

Examples of suitable α- or β-hydroxyketones for reaction with the enol-ethers are benzoin, α-methyl-benzoin, α-methylol-benzoin methyl ether, αmethylol-benzoin isopropyl ether, 2,2′-dichlorobenzoin and 4,4′-dichlorobenzoin. The reaction of benzoin is preferred.

The α,β-olefinically unsaturated ethers are generally employed in amounts of 1 and 2 moles per mole of the benzoin compound; examples of suitable ethers are openchain enol-ethers, such as vinyl alkyl ethers, especially vinyl ethyl ether and vinyl isobutyl ether, or, advantageously, cyclic enol-ethers, such as those of the structure

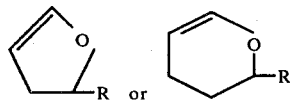

in which R is H or alkoxy, in particular 3,4-dihydro-2H-pyran and 2-methoxy-2,3-dihydro-4H-pyran.

The acetals obtained by the unsaturated ether undergoing an addition reaction at the hydroxyl group of the α- or β-hydroxyketones are obtained in a form which can readily be isolated and in yields which frequently exceed 90% of theory; they are in some cases crystalline and in some cases oily, distillable compounds, which are always in the form of mixtures of the diastereomers to be expected. Proof of the fact that one is dealing with diastereomer mixtures, and proof of the structure of the diastereomers, can be provided particularly conclusively by the NMR-spectra. Examples of acetals according to the invention are benzointetrahydropyranyl ether, α-methyl-benzointetrahydropyranyl ether, benzoin 2-methoxy-tetrahydropyranyl ether, the tetrahydropyranyl ether of α-methylol-benzoin methyl ether and isopropyl ether, acetaldehyde-ethyl-(α-benzoyl-benzyl)-acetal (from benzoin and vinyl ethyl ether), acetaldehyde-isopropyl-(α-benzoyl-benzyl)-acetal (from benzoin and vinyl isopropyl ether), and the corresponding reaction products from 4,4′-dichlorobenzoin, 2,2′-dichlorobenzoin and α-methoxybenzoin and vinyl ether, vinyl butyl ether, vinyl isobutyl ether, 3,4-dihydro-2H-pyran, 2-methoxy-2,3-dihydro-4H-pyran and 2,3-dihydrofuran.

The new compounds manufactured according to the invention display very good reactivity when used as photoinitiators for monomers possessing at least one photopolymerizable carbon-carbon multiple bond and mixtures of such monomers with one another and/or the known additives and are superior in the respect to, for example, benzoin isopropyl ether, which finds application in practice.

Very suitable photopolymerizable monomers are compounds and substances with carbon-carbon double bonds which are activated by, for example, aryl, carbonyl, amide, ester, carboxyl or nitrile groups, halogen atoms or carbon-carbon double bonds or carbon-carbon triple bonds. Styrene, vinyltoluene, acrylic acid and methacrylic acid and their esters, nitriles and amides, for example acrylamide, N-methylolacrylamide, diethers from 1 mole of glycol and 2 moles of N-methylolacrylamide, methyl methacrylate, methylene-bis-acrylamide and m-xylylene-bis-acrylamide may be mentioned as examples.

The photopolymerizable compounds can readily be chosen by those skilled in the art to suit the particular end use of the mixtures and can contain, in a known manner, unsaturated and/or saturated polymers and/or further known additives, such as inhibitors against thermal polymerization, for example hydroquinone or tert.-butylhydroquinone, skinforming substances such as paraffin, flow improvers such as silicone oil, fillers and/or pigments or dyestuffs, these substances being added in the customary amounts.

Such mixtures are known to those skilled in the art and the nature and amount of the additives depend in particular on the end use of the mixtures.

The compounds according to the invention are particularly suitable for use with photopolymerizable compositions which lend themselves to the manufacture of systems for optical information fixing, especially to the production of photopolymer printing plates and amongst these especially the preparation of relief printing plates by image-wise exposure of layers of photopolymerizable mixtures and subsequent elution of the unexposed parts of the layer. Suitable mixtures containing compounds with at least one polymerizable carbon-carbon multiple bond are mixtures which contain about 10 to 60% by weight, and preferably 20 to 35% by weight, of monomers which predominantly have at least two photopolymerizable carbon-carbon multiple bonds, such as diacrylates, dimethacrylates, bisacrylamides and bismethacrylamides of aliphatic or aromatic diamines with 2 to 8 carbon atoms, and monomers which optionally contain urethane or urea groups in addition to amide groups, and 90 to 40% by weight, and preferably 80 to 65% by weight, of polymer soluble in an organic solvent, such as an alcohol, a ketone or an ether. Examples of polymers which can be used are copolyamides, such as copolyamides of ε-caprolactam, hexamethylene-diammonium adipate and p,p'-diaminodicyclohexyl-methane adipate, and also soluble polyurethans, polyureas, polyethers or soluble cellulose derivatives. The details of such mixtures and their processing, described in the known patent literature, particularly in British Patent Nos. 1,154,384, 1,173,043 and 1,191,177 or Belgian Patent No. 794,260, suffices for those skilled in the art.

Further examples of uses of the compounds of the invention are as photoinitiators for the customary unsaturated polyester resins, that is to say mixtures of unsaturated polyesters and copolymerizable monomers, such as styrene, which serve for the production of coatings which can be cured by ultraviolet irradiation, and photoinitiators for the manufacture of holograms, photo-resist lacquers and photocuring printing inks. In general, the photoinitiator are used for these purposes in amounts of about 0.01 to 6% by weight, and especially 0.05 to 4% by weight, relative to the photosensitive mixture.

The radiation sources for the light which initiates the polymerization of such mixtures are sources which emit light of wavelengths between 230 and 450 nm. Above all, radiation sources with emission maxima in the range of 300 to 380 nm, or sources which emit a sufficiently high proportion of light of this wavelength range, are used. Mercury medium pressure lamps are particularly suitable, but mercury high pressure lamps and mercury low pressure lamps and super-actinic fluorescent tubes are also suitable. The lamps mentioned can optionally be doped.

Unless otherwise stated, the parts and percentages indicated in the example which follow are units by weight. The relationship between parts by volume and parts is as of one liter to one kilogram.

EXAMPLE 1

0.05 part of p-toluenesulfonic acid is added to a suspension of 58.1 parts of benzoin in 80 parts by volume of benzene in the dark, and 33.9 parts (approx. a 50% molar excess) of 3,4-dihydro-2H-pyran are then added dropwise over half on hour, whilst stirring. The reaction mixture is subsequently stirred for half an hour at 50° to 55° C, 2 parts of powdered potassium carbonate are added and the mixture is stirred for a further 2 hours at room temperature. After filtration, and stripping off the solvent under reduced pressure, 85.5 parts (93% of theory) of pale yellow crystals are obtained; these are benzoin tetrahydropyranyl ether, as is shown by the spectrum and analysis. After recrystallisation from petroleum ether the substance is colorless and crystalline, melts at 67.5° to 77° C, and has the following NMR spectrum (measured in CDCl₃; all values of the chemical shift δ are rounded off to 0.05 ppm):

$\delta = 1.1 - 2.2$ (multiplet, 6 protons)
3.3 –4.0 (2 multiplets, 2 protons)
4.6 –4.9 (2 pseudo-triplets, 1 proton)
6.0 –6.15 (2 singlets, 1 proton)
7.0 –7.65 (multiplet, 8 protons)
7.8 –8.2 (multiplet, 2 protons).

The NMR spectrum shows that the product is the expected mixture of the two diastereomers in the ratio of about 1:1.

EXAMPLE 2

Analogously to Example 1, δ-methylbenzoin and 3,4-dihydro-2H-pyran give α-methylbenzoin tetrahydropyranyl ether as a crystalline substance melting over the range of 90° to 98° C. The yield is 81% of theory.
NMR spectrum (in CDCl₃):
$\delta = 1.0 - 2.15$ (multiplet, 6 protons)
1.8 (2 coincident singlets, 3 protons)
3.1 –3.6 (2 multiplets, 2 protons)
4.55 –5.0 (2 multiplets, 1 proton)
6.8 –7.6 (multiplet, 8 protons)
7.7 –8.1 (multiplet, 2 protons)

The NMR spectrum shows that the two diastereomers which were to be expected are present in the ratio of about 2:1.

EXAMPLE 3

82 parts of p-anisoin are reacted with 34 parts of 3,4-dihydro-2H-pyran (approx. 35% molar excess) in 500 parts by volume of benzene, analogeously to Example 1. p-anisoin tetrahydropyranyl ether is obtained in a yield of 71.6% and melts over the range of 96° to 102° C.
NMR spectrum (in CDCl₃):
$\delta = 1.1 - 2.2$ (multiplet, 6 protons)
3.3 –4.1 (multiplet, 2 protons)
3.7 –3.85 (4 singlets, 6 protons)
4.65 –4.9 (2 multiplets, 1 proton)
5.95 –6.1 (2 singlets, 1 proton)
6.7 –7.1 (multiplet, 4 protons)
7.3 –7.6 (multiplet, 2 protons)
7.9 –8.2 (multiplet, 2 protons)

According to the NMR spectrum, the two diastereomers are present in the ratio of about 4:1.

EXAMPLE 4

Analogously to Example 1, α-methylol-benzoin methyl ether and 3,4-dihydro-2H-pyran give the tetrahydropyranyl ether of α-methylolbenzoin methyl ether, having the following structure

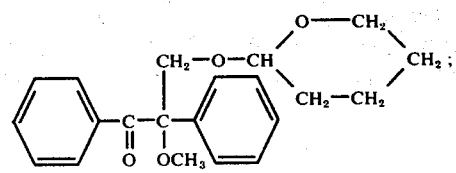

this is a crystalline substance of melting point 53° to 62° C and is produced in a yield of 97% of theory.
NMR spectrum (in CDCl₃):

| | | |
|---|---|---|
| δ = | 1.0 – 2.3 | (multiplet, 6 protons) |
| | 2.9 – 3.9 | (2 multiplets, 2 protons) |
| | 3.3 – 3.4 | (2 singlets, 3 protons) |
| | 4.3 – 4.7 | (2 multiplets, 1 proton |
| | 4.25 | (double doublet degraded to a singlet) } 2 protons) |
| | 3.95 and 4.5 | (double doublet, τ= 11 Hz) |
| | 7.1 – 7.7 | (multiplet, 8 protons) |

7.9 – 8.1 (multiplet, 2 protons)

The NMR spectrum indicates a mixture of 2 diastereomers in the ratio of about 1:1.

EXAMPLE 5

85 parts of benzoin are reacted with 68.4 parts (50% molar excess) of 2-methoxy-2,3-dihydro-4H-pyran in 120 parts by volume of benzene, analogously to Example 1. The resulting benzoin 2-methoxy-tetrahydropyranyl ether, obtained in a yield of 87.4% of theory, boils at 195° to 200° C/0.3 mm Hg and has the following structure:

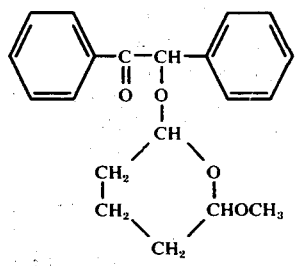

NMR spectrum (in CDCl$_3$):
δ = 1.0 –2.4 (multiplet, 6 protons)
3.1 –3.55 (4 singlets, 3 protons)
4.5 –4.9 (multiplet, 1 proton)
4.9 –5.2 (multiplet, 1 proton)
5.9 –6.3 (4 singlets, 1 proton)
6.9 –7.7 (multiplet, 8 protons)
7.8 –8.25 (multiplet, 2 protons)

The NMR spectrum shows the presence of the 4 expected diastereomers; the two main components are present in the ratio of about 1.3:1.

EXAMPLE 6

0.2 part of p-toluenesulfonic acid is added to a suspension of 170 parts of benzoin in 240 parts by volume of benzene; 74.75 parts (24% molar excess) of vinyl ethyl ether and then added dropwise over 45 minutes at 50° to 55° C, whilst stirring. The mixture is stirred for a further 5 minutes at the stated temperature and then cooled to room temperature, and after adding 40 g of powdered potassium carbonate the mixture is stirred for a further 6 hours. After filtration, stripping off the solvent and distillation, 211 parts (92.7% of theory) of acetaldehyde-ethyl-(α-benzoyl-benzyl)-acetal of the structure.

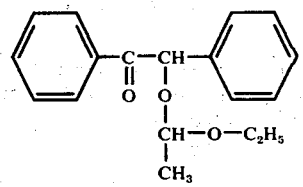

are obtained; the compound boils at 163° to 165° C/0.25 mm Hg.
NMR spectrum (in CDCl$_3$):
δ = 0.9 –1.25 (multiplet, 3 protons)
1.2 –1.5 (2 overlapping doublets, 3 protons)
3.2 –3.75 (multiplet, 2 protons)
4.75 –5.05 (2 overlapping quartets, 1 proton)
5.95 and 6.05 (2 singlets, 1 proton)
6.9 –7.7 (multiplet, 8 protons)
7.85 –8.2 (multiplet, 2 protons)
According to the NMR spectrum, the diastereomers are present in the ratio of about 1.2:1 in the mixture.

EXAMPLE 7

The procedure followed is analogous to Example 6 but instead of vinyl ethyl ether 118.8 parts (55% molar excess) of vinyl isobutyl ether are employed. Acetaldehydeisobutyl-(α-benzoyl-benzyl)-acetal is obtained in a yield of 88.5% of theory; the substance boils at 169° to 172° C/0.3 mm Hg and has the following structure:

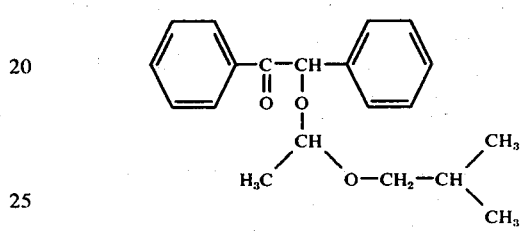

NMR spectrum (in CDCl$_3$):
δ = 0.6 –1.0 (multiplet, 6 protons)
1.2 –1.45 (2 overlapping doublets, 3 protons)
1.5 –3.1 (2 overlapping multiplets, 1 proton)
3.0 –3.45 (multiplet, 2 protons)
4.7 –5.05 (multiplet, 1 proton)
5.95 and 6.05 (2 singlets, 1 proton)
7.0 –7.65 (multiplet, 8 protons)
7.8 –8.2 (multiplet, 2 protons)
The NMR spectrum shows the two expected diastereomers in the ratio of about 1.4:1.

EXAMPLE 8

1 part of benzoin tetrahydropyranyl ether is added to a solution of 60 parts of a polyamide from about equal parts of hexamethylene-diammonium adipate, 4,4'-diamino-dicyclohexyl-methane adipate and ε-caprolactam, which is soluble in aqueous alcohol, 30 parts of the diether from 2 moles of N-methylolacrylamide and 1 mole of ethylene glycol and 0.2 part of the potassium salt of N-nitroso-N-cyclohexylhydroxylamine. The solution is cast to give a film and the latter is pressed onto a metallic substrate provided with a light-absorbing adhesive coating.

The coated, light-sensitive plate is exposed with its surface in contact with a negative. Fluorescent tubes with a high proportion of ultraviolet light, at a distance of 3 cm from the plate to be exposed, are used as the light source. After exposure, the unexposed parts of the plate are dissolved out with a mixture of 80 parts of ethanol and 20 parts of water. After drying, a printing plate with a sharp relief is obtained.

EXAMPLE 9

An unsaturated polyester is manufactured by esterifying 431 part of maleic anhydride and 325 parts of phthalic anhydride with 525 parts of 1,2-propylene glycol. After adding 0.01% of hydroquinone, a 66% strength solution of the polyester in styrene is prepared. 97 parts of this unsaturated polyester resin are mixed with 3 parts of benzoin tetrahydropyranyl ether.

For the photocuring experiments, 10 parts of a 1% strength solution of paraffin (softening range 50° to 52° C) in styrene were added to 100 parts of this mixture and the resin was applied to glass plates by means of a film spreader with a 400 μm gap. After allowing evaporation for about one minute, the films were exposed for 5 minutes to fluorescent lamps (Phillips TLA 05/40 W), mounted at a distance of 4 cm.

After an exposure time of 5 minutes, the films had a pendulum hardness (measured by König's method) of 112 seconds and can therefore be rubbed down and buffed.

We claim:

1. Acetals of benzoin compounds which act as photoinitiators and which have the formula

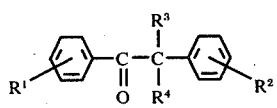

which contain at least one acetal group

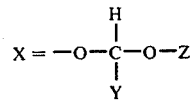

in the radicals $R^3$ or $R^4$, Y being $CH_3$ and Z being $C_2$–$C_4$-alkyl, or Y and Z together forming a propylene or butylene group; $R^1$ and $R^2$ are H, $C_1$–$C_4$-alkyl, $C_1$–$C_4$-alkoxy or Cl, $R^3$ is H, $CH_3$, $CH_2OR^5$ or $CH_2X$, $R^4$ is X or $OR^5$ and $R^5$ is $C_1$–$C_6$-alkyl.

2. An acetal as set forth in claim 1 wherein $R^3$ is H, $R^4$ is X, and Z and Y are joined to form a tetrahydropyranyl ether ring.

3. A compound as set forth in claim 1 wherein said acetal is benzointetrahydropyranyl ether.

4. A compound as set forth in claim 1 wherein said acetal is α-methyl-benzointetrahydropyranyl ether.

5. A compound as set forth in claim 1 wherein said acetal is benzoin 2-methoxy-tetrahydropyranyl ether.

* * * * *